United States Patent [19]
Gloor

[11] Patent Number: 5,596,901
[45] Date of Patent: Jan. 28, 1997

[54] METHOD FOR THE ABSOLUTE MEASUREMENT OF THE TEARING STRENGTH OF FIBRES

[75] Inventor: RenéGloor, Schöneberg, Switzerland

[73] Assignee: Zellweger Luwa AG, Uster, Switzerland

[21] Appl. No.: 532,613

[22] PCT Filed: Jan. 26, 1995

[86] PCT No.: PCT/CH95/00018

§ 371 Date: Oct. 10, 1995

§ 102(e) Date: Oct. 10, 1995

[87] PCT Pub. No.: WO95/22044

PCT Pub. Date: Aug. 17, 1995

[30] Foreign Application Priority Data

Feb. 10, 1994 [CH] Switzerland ................. 395/94

[51] Int. Cl.⁶ .................................................. G01L 5/04
[52] U.S. Cl. ..................................... 73/159; 73/830
[58] Field of Search ........................ 73/159, 830, 835, 73/866

[56] References Cited

U.S. PATENT DOCUMENTS

| | | |
|---|---|---|
| 1,932,682 | 10/1933 | Beckley . |
| 3,777,557 | 12/1973 | Dunlap et al. ............... 73/830 X |
| 4,391,153 | 7/1983 | Taylor . |
| 4,885,823 | 12/1989 | Voellm . |
| 4,980,951 | 1/1991 | Gloor et al. . |
| 5,050,437 | 9/1991 | Etter ................................ 73/830 |
| 5,076,104 | 12/1991 | Glaesemann et al. ............ 73/830 |
| 5,167,150 | 12/1992 | Shofner et al. . |
| 5,185,639 | 2/1993 | Toedtli et al. ................... 73/159 X |
| 5,237,389 | 8/1993 | Hartrumpf . |
| 5,295,401 | 3/1994 | Toedtli ............................ 73/159 X |

*Primary Examiner*—Sandra L. O'Shea
*Assistant Examiner*—Elizabeth L. Dougherty
*Attorney, Agent, or Firm*—Burns, Doane, Swecker & Mathis, LLP

[57] ABSTRACT

The method for measuring the tearing strength of fibers, especially of textile fibers, comprises the following steps:

A) the fibers to be measured or part regions of such fibers are treated to form a single-layer planar fiber tuft (1);

B) the fiber tuft (1) is clamped in the fiber plane (13) perpendicularly to the fiber direction along two parallel lines (18, 19) having a predetermined clearance;

C) the cross-section of the class (12) of fibers clamped between the two lines (18, 19) is determined individually and summed to form the total cross-section;

D) the fiber tuft (1) is pulled apart to tear by the application of a force in the fiber plane (13) in the direction of the arrow (14) between the two lines (18, 19);

E) the tearing strength is determined from the tearing force occurring and the total cross-section determined.

10 Claims, 4 Drawing Sheets

METHOD FOR THE ABSOLUTE MEASUREMENT OF THE TEARING STRENGTH OF FIBRES

The invention relates to a method according to the pre-characterizing clause of Patent claim 1.

In textile technology, the measurement of the tearing strength of textile fibres yields important information on the problems to be expected in spinning and on the achievable yarn strength.

Classic methods for determining the tearing strength on the individual fibre are already known. However, there are no measuring instruments of wider application for these methods on the market. One example of such a method is described in U.S. Pat. No. 5,167,150 SHOFNER ET AL.

The measuring instruments commonly found on the market are based on the measurement of the bundle tearing strength. The most important instruments are known by the trade names Pressley, Stelometer and HVI.

In the measurement of the so-called Pressley index, a well combed-out and parallelized fibre bundle is gripped in the jaws of two clamps. There is no clearance between the two clamps. The fibres projecting beyond the clamps are cut off. A sliding weight on a load arm increases the force until the fibre bundle is torn apart. The load at tear can thereupon be read off on a load arm. The fibre bundle is subsequently weighed. The Pressley index is then calculated from the weight and the load at tear.

The Stelometer functions in the same way as the Pressley instrument. However, the clearance between the clamps is not 0, but ⅛ inch. Statements can consequently also be made on the elongation of the fibres.

The HVI are largely based on the Stelometer arrangement. In these fully automatic measuring instruments, the fibre bundle cannot be weighed for various reasons. In the tensile test, a force sensor measures the maximum tearing force at this point. The location of the constant mass point within the fibre tuft is established by means of an additional sensor. This mass-point measurement does not yield any absolute indication of the number of fibres, the fibre weight or the fibre cross-section. The constant mass point is calibrated by means of a calibrating cotton, of which the tearing force in g/tex (grams per tex/according to DIN standards 60905, 60910) is known. The dispersion of the calibrating cotton and the accuracy in the measurement of the desired values influence the dispersion between the measuring instruments and the reproducibility of the individual measuring instruments. The fibre tuft is moved between the detection of the mass point and the actual tearing-strength measurement. At the same time, the fibre tuft can vary according to the fibre properties, thus leading to increased dispersions as a result of mass-point deviations. The calibration constitutes considerable expenditure of time which is an important factor in these measuring instruments trimmed for speed. The functioning of the HVI is already known from various measuring instruments.

In all the known methods for measuring the bundle tearing strength, the actually torn fibre cross-section is approximated only indirectly. Wide dispersions of the measurement results occur thereby. A further disadvantage is that the crimping of the fibres is not eliminated, that is to say the point in time of the fibre break is greatly influenced by the individual crimping of each fibre. The measured bundle tearing strength is therefore closely associated with the particular crimping.

The invention is intended to remedy this. The object on which the invention is based is to provide a method for measuring the tearing strength of fibres, especially of textile fibres, which is based on an absolute measuring method.

The invention achieves the set object by means of a method which has the features of claim 1.

The method according to the invention eliminates the disadvantages of the state of the art and is characterized by an absolute measuring method which avoids the use of calibrating cotton.

Further advantageous embodiments of the invention are characterized in the dependent claims.

The invention and developments of the invention are explained in more detail below by means of the partially diagrammatic representations of an exemplary embodiment.

The method according to the invention is discussed in detail below with reference to FIGS. 1 to 5.

To prepare the fibre sample, it is first treated by means of a known opening module, for example according to EP-B1 393,360 GLOOR, and an instrument for the alignment of fibres known by the trade name "Fibroliner" of the company Siegfried Peyer AG (EP-B1 294,571 VÖLLM), to form an ordered-end representative thin single-layer fibre tuft.

Figure 1:
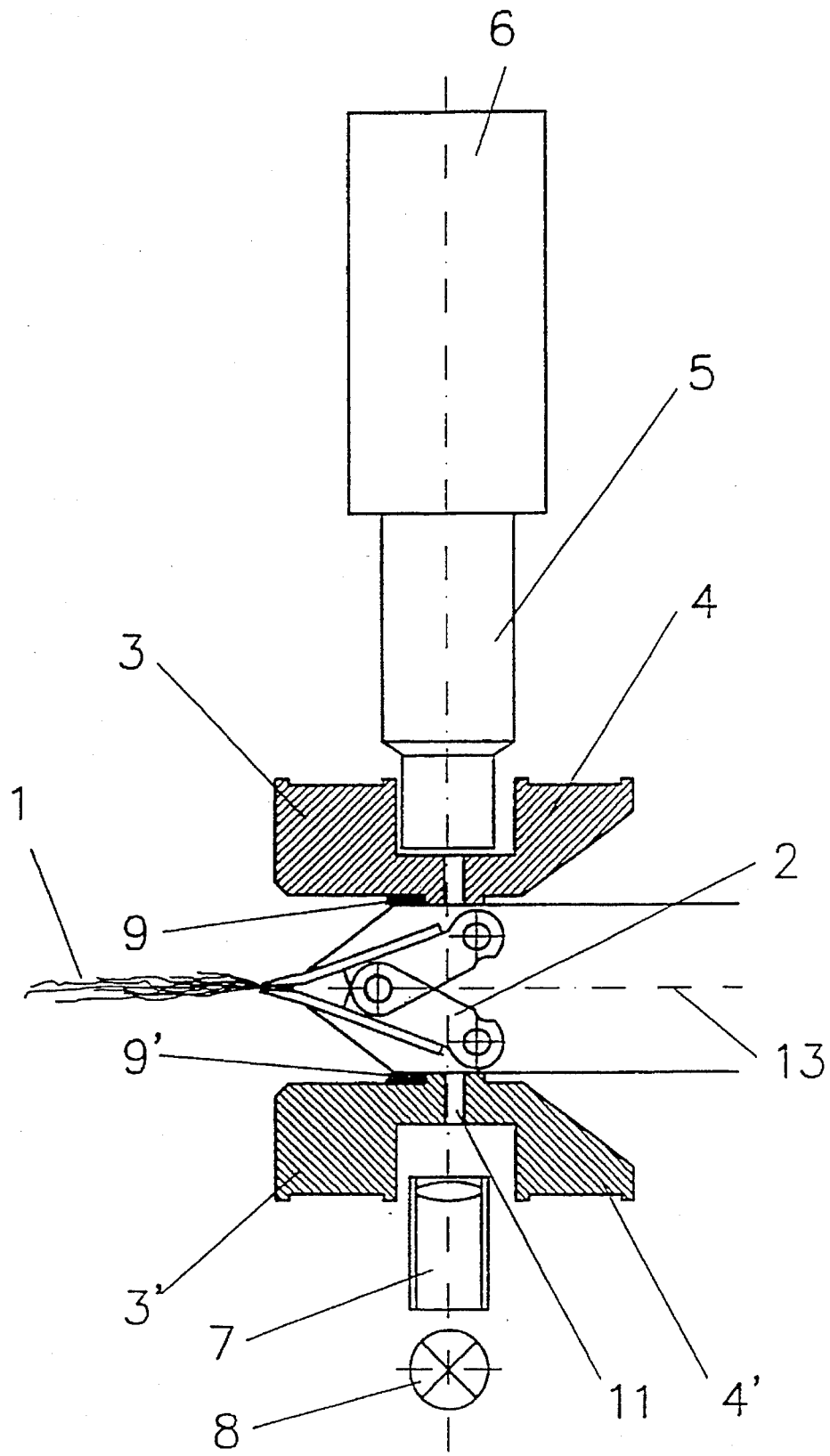
FIG. 1 shows a diagrammatic longitudinal section through an appliance for carrying out the method according to the invention, with an open tearing module.

As shown in FIG. 1, the ordered-end fibre tuft 1, which is held by the gripper 2, is transported by the needle bed of the "Fibroliner" to the open tearing module 3, 3', 4, 4'. As soon as the gripper 2 leaves the tearing module 3, 3', 4, 4', the gripper jaws 3, 4 and 3', 4' begin to close automatically. The stretching device 9, for example in the form of a brush, felt, porous plastic, leather or fabric, removes the crimping of each fibre by providing the individual fibres of the fibre tuft 1 with a minimal pretension. When the fibre tuft 1 has reached the tearing position which is defined at a fixed length or in dependence on the length distribution, the gripper jaws 3, 4 and 3' 4' are loaded with a clamping force of approximately 400N.

Figure 2:
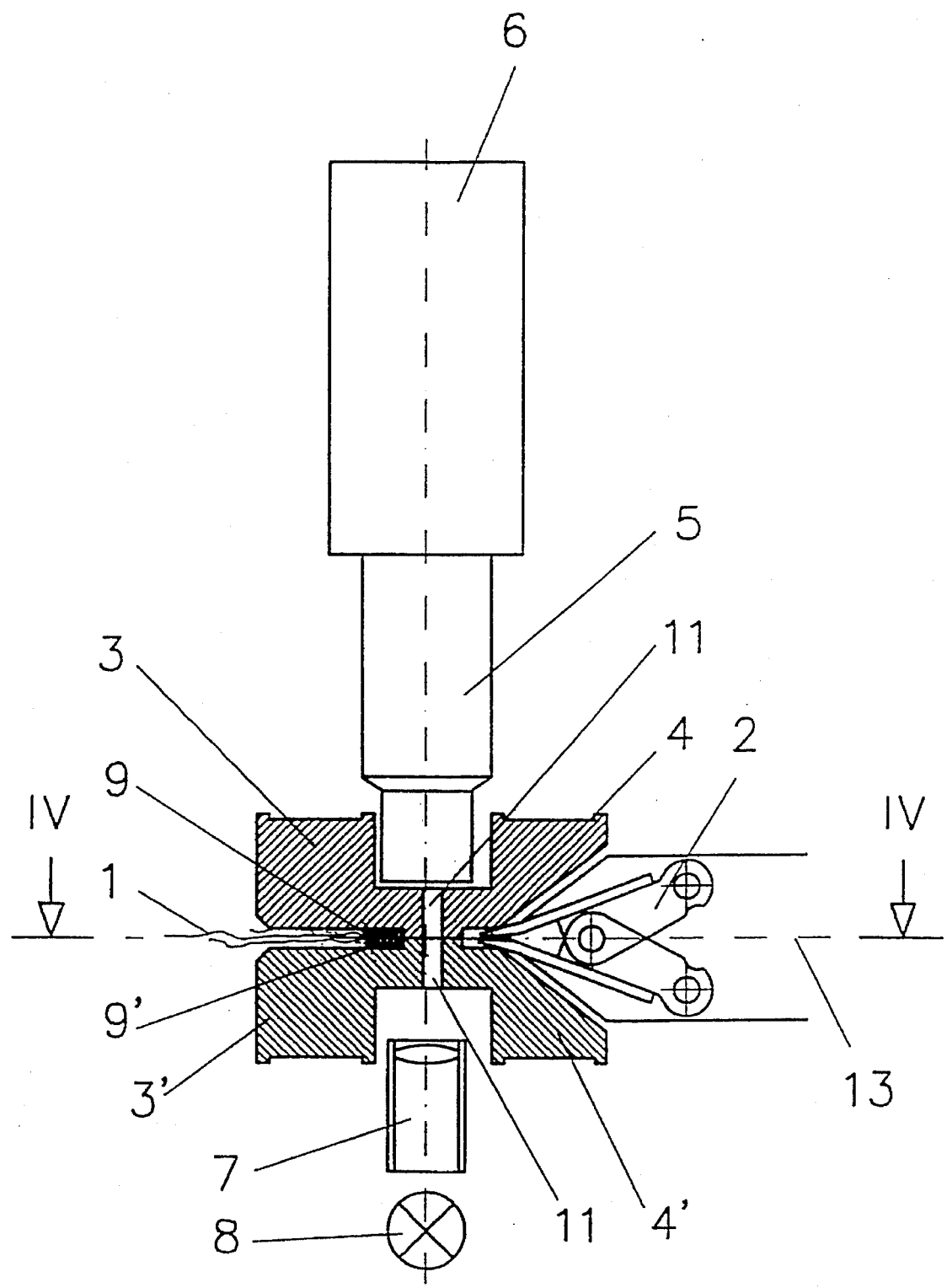
FIG. 2 shows a diagrammatic longitudinal section through an appliance for carrying out the method according to the invention, with a closed tearing module.

As shown in FIG. 2, the fibre tuft 1 is then ready for the tearing-force measurement. In order to measure the thickness of the individual fibres, a lighting objective 7 with lighting 8, an imaging objective 5 and a CCD camera 6 are provided. This imaging unit 5, 6, 7, 8 moves as a whole in a plane parallel to the fibre plane 13 transversely relative to the fibres and measures the thickness of each individual fibre of the fibre tuft 1. The clearance 11 between the gripper jaws 3, 4 and 3', 4' is typically ⅛ inch.

Figure 3:
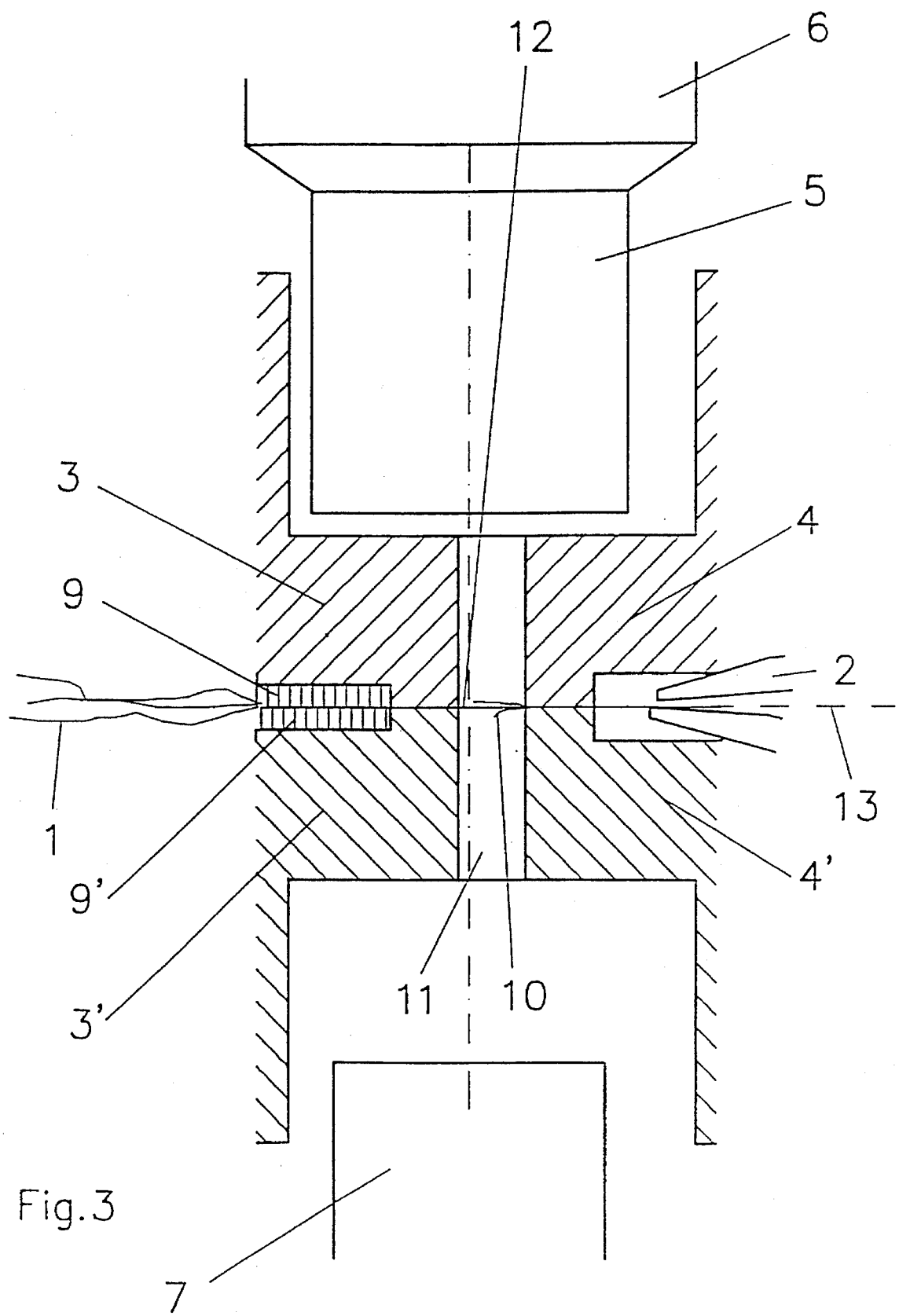
FIG. 3 shows an enlarged cutout from FIG. 2.

As shown in FIG. 3, the measurement of the fibre thickness takes place as near as possible to the gripper jaw 3, 3'. Two different classes of fibres are located between the gripper jaws 3, 4 and 3', 4'. One class 12 consists of those fibres which are clamped by both gripper jaws 3, 4 and 3', 4' and which are torn apart during the tearing-force measurement. The other class 10 comprises those fibres which end within the clearance 11 and which are retained only by the gripper jaws 4, 4'. This class 10 of fibres has no influence on the tearing-force measurement. These unequivocal conditions occur as a result of the ordering of the end of the fibre tuft 1. If the thickness measurement takes place as near as possible to the gripper jaw 3, 3', the number and cross-section of the fibres torn apart can be determined with great accuracy.

Figure 4:
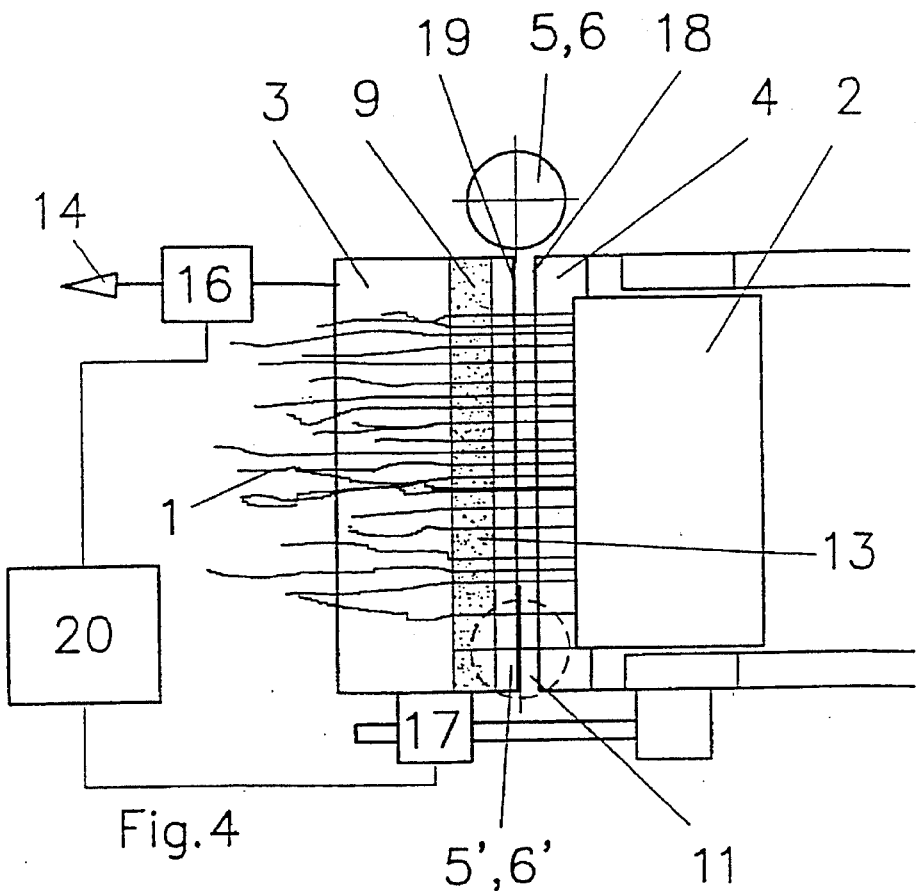
FIG. 4 shows a cross-section along the line IV—IV through FIG. 2 before the tearing.

FIG. 4 shows the fibres of the fibre tuft 1 which are introduced free of crimping in the closed tearing module 3, 4 and the movement of the CCD camera 6 with imaging objective 5 from the initial position transversely to the individual fibres into the end position 5', 6'. The gripper jaw 3 (which clamps the fibres by means of the counterpiece 3' located above the drawing plane) is then moved apart at a constant speed in the direction of the arrow 14.

The built-in force sensor 16 records the tensile force occurring and a distance sensor 17 measures the distance covered by the gripper jaw 3.

Figure 5:
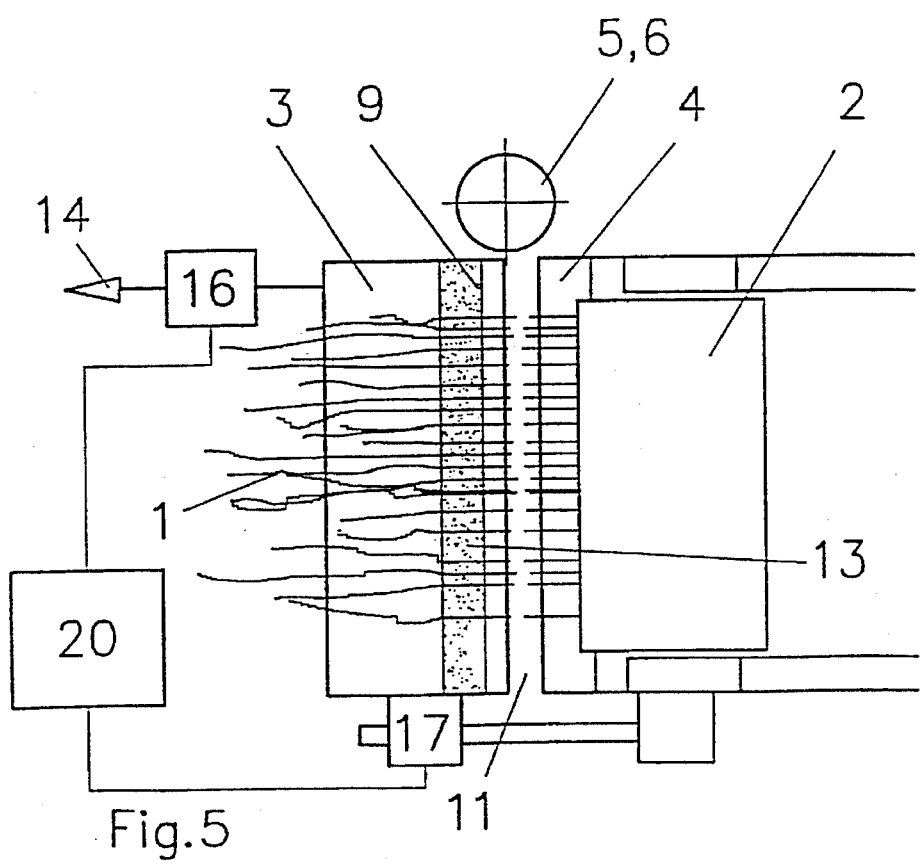
FIG. 5 shows a cross-section along the line IV—IV through FIG. 2 after the tearing.

FIG. 5 shows the torn-apart fibre tuft 1 before it is removed from the tearing module 3, 4. The trend of the measured tensile-force curve and the results of the thickness measurement give a maximum tensile force at tear in the dimension [$Nmm^{-2}$]. This value can be converted to the dimension [g/tex] by means of the appropriate constants in the computer 20.

As a result of the correct recording of the force, of the fibre cross-section and of the elimination of the fibre crimping, the tearing force can be measured absolutely without the use of a calibrating cotton.

The results of the thickness measurement can, of course, not only be used for measuring the tearing strength. The fibre fineness is an accepted, important parameter in textile technology. The method according to the invention therefore has the further advantage that other parameters, such as, for example, the fibre fineness, degree of ripeness, helix, can also be measured at the same time with high accuracy.

A disturbance factor which influences the fibre strength is moisture. The recording and consideration of the water content increase the reproduceability of the measurement results. In a preferred embodiment of the method according to the invention, therefore, before the measurement of the tearing strength, the length distribution of the fibre tuft 1 is measured in a capacitive measuring field. An instrument suitable for this purpose is the "Almeter" (the company Siegfried Peyer AG) which measures capacitively the length distribution of an ordered-end fibre tuft.

The variation in the dielectric leads to a change in the capacitance of the measuring capacitor. The dielectric is influenced ten times more by the water present in the moist fibres, for example of cotton, than by the cellulose. The absolute change in capacitance is thus based largely on the water content and on the number of fibres present. In contrast, the optical thickness measurement is influenced only marginally by the moisture. The difference between the optical thickness measurement and the capacitive measurement gives a good measure of the water content. A tearing force independent of moisture can be determined by means of this additional parameter.

I claim:

1. Method for measuring the tearing strength of fibres, especially of textile fibres, comprising the following steps:

A) the fibres to be measured or part regions of such fibres are treated to form a single-layer planar fibre tuft (1);

B) the fibre tuft (1) is clamped in the fibre plane (13) perpendicularly to the fibre direction along two parallel lines (18, 19) having a predetermined clearance;

C) the cross-section of the fibres clamped between the two lines (18, 19) is determined individually and summed to form the total cross-section;

D) the fibre tuft (1) is pulled apart to tear the fibres clamped between the two lines (18, 19) by the application of a force in the fibre plane (13) in a direction perpendicular to the two lines (18, 19);

E) the tearing strength is determined from the tearing force occurring and the total cross-section determined.

2. Method according to claim 1, wherein, before the tearing, the fibres of the fibre tuft (1) are provided with a minimum pretension, so that they are free of crimping.

3. Method according to claim 1, wherein the measurement of the cross-section of the fibres takes place in that the fibre tuft (1) is brought between a lighting objective (7) with lighting (8) and an imaging objective (5) and the image perpendicular to the fibre plane (13) and generated by the imaging optics is fed to a camera (6).

4. Method according to claim 3, wherein the camera (6) is moved in steps from individual fibre to individual fibre over the entire width of the fibre tuft (1).

5. Method according to claim 1, wherein the fibres of the fibre tuft (1) are clamped along the lines (18, 19) by means of gripper jaws (3, 4, 3', 4').

6. Method according to claim 5, wherein the measurement of the cross-section of the fibres takes place as near as possible along the line (19) of the gripper jaw (3, 3') which clamps the smaller number of individual fibres.

7. Method according to claim 5, wherein the clearance between the gripper jaws (3, 4, 3', 4') is between 1 and 5 mm, preferably between 2.5 and 3.5 mm.

8. Method according to claim 1, characterized by the following additional steps which take place before the measurement of the tearing strength:

F) the length distribution of the fibre tuft (1) is measured in a capacitive measuring field;

G) the water content of the fibres is determined from the difference between the optical thickness measurement according to step C) and the capacitive measurement; and H) the tearing strength independent of moisture is determined from the tearing force occurring, the total cross-section determined and the measured water content.

9. Method according to claim 1, wherein the fibres to be measured in step A or part regions of such fibres are treated to form an ordered-end fibre tuft (1).

10. An apparatus for measuring the tearing strength of fibres, especially of textile fibres, comprising:

a) gripper jaws between which a single-layer planar fibre tuft is clamped and torn apart in the fibre plane perpendicularly to the fibre direction along two parallel lines having a predetermined clearance;

b) a lighting objective with lighting, and an imaging objective the beam path of which is arranged so as to be displaceable perpendicularly to the fibre plane of the gripper jaws;

c) a camera, to which the image generated by the imaging objective is fed;

d) a force sensor serving for measuring the tearing force occurring between the gripper jaws; and e) a computer;

wherein the fibres to be measured or part regions of such fibres are treated to form the single-layer planar fibre tuft; the fibre tuft is clamped in the fibre plane perpendicularly to the fibre direction along two parallel lines having a predetermined clearance; the cross-section of the class of fibres clamped between the two lines is determined individually and summed to form the total cross-section; the fibre tuft is pulled apart to tear by the application of a force in the fibre plane in the direction of the arrow between the two lines; and the tearing strength is determined from the tearing force occurring and the total cross-section determined.

* * * * *